(12) United States Patent
Saito et al.

(10) Patent No.: US 6,387,392 B1
(45) Date of Patent: May 14, 2002

(54) INTRAORAL ADHESIVE PREPARATION

(75) Inventors: Junichi Saito; Kazuhisa Ninomiya, both of Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 0 days.

(21) Appl. No.: 09/935,437

(22) Filed: Aug. 23, 2001

(30) Foreign Application Priority Data

Aug. 24, 2000 (JP) ........................................ 2000-254434

(51) Int. Cl.$^7$ ................................................. A61F 13/00
(52) U.S. Cl. ...................................................... 424/435
(58) Field of Search .......................................... 424/435

(56) References Cited

U.S. PATENT DOCUMENTS 4,597,960 A * 7/1986 Cohen ........................... 424/28
6,139,861 A * 10/2000 Friedman ...................... 424/435

* cited by examiner

*Primary Examiner*—Raymond Henley, III
(74) *Attorney, Agent, or Firm*—Leydig, Voit & Mayer, Ltd.

(57) ABSTRACT

An intraoral adhesive preparation is provided, which has a support made of a cloth, and a pressure-sensitive adhesive layer containing a drug, which is formed on one surface of the support, wherein the dissolution of the drug into water from the surface of the support, which surface being free of a pressure-sensitive adhesive layer, after immersion in water at 32° C. for 20 minutes, is not more than 25 wt % of the total content of the drug.

7 Claims, 2 Drawing Sheets

INTRAORAL ADHESIVE PREPARATION

TECHNICAL FIELD OF THE INVENTION

The present invention relates to an adhesive preparation to be applied in the oral cavity for intraoral administration of a drug.

BACKGROUND OF THE INVENTION

Conventional preparations for intraoral drug administration include liquid, ointment, jelly, spray, troche, buccal tablet, sublingual tablet and the like.

In these preparations, unnecessary leakage of a drug into saliva and migration of the drug into the sites where the drug is not needed is inevitable, because the solution flows, base materials of ointment and jelly dissolve, a spray may be excessively applied and for other reasons. As a result, these preparations are associated with problems in that patients unnecessarily suffer from uncomfortableness, such as bitterness and the like, the rate of utilization of the drug decreases, preventing sufficient drug efficacy, and the like.

SUMMARY OF THE INVENTION

In view of the above, the present invention aims at providing an intraoral adhesive preparation, which is less associated with drug leakage into saliva etc., and the like, which does not taste unnecessarily bitter for patients, and which does not decrease the rate of utilization of the drug.

Accordingly, the present invention provides the following.

An intraoral adhesive preparation comprising a support made of a cloth and a pressure-sensitive adhesive layer containing a drug, which is formed on one surface of the support, wherein the dissolution of the drug into water from the surface of the support, which surface being free of a pressure-sensitive adhesive layer, after immersion in water at 32° C. for 20 minutes, is not more than 25 wt % of the total content of the drug. This achieves the above-mentioned object.

In a preferable embodiment, the cloth has a mass of 20–150 g/m$^2$, and/or a thickness of 0.1–1.0 mm.

In a preferable embodiment, the cloth is a nonwoven fabric, more preferably a nonwoven fabric, which is produced by a spun-lace method and/or is made mainly of a polyolefin fiber.

In a preferable embodiment, the drug is a local anesthetic.

DETAILED DESCRIPTION OF THE INVENTION

Figure 1:
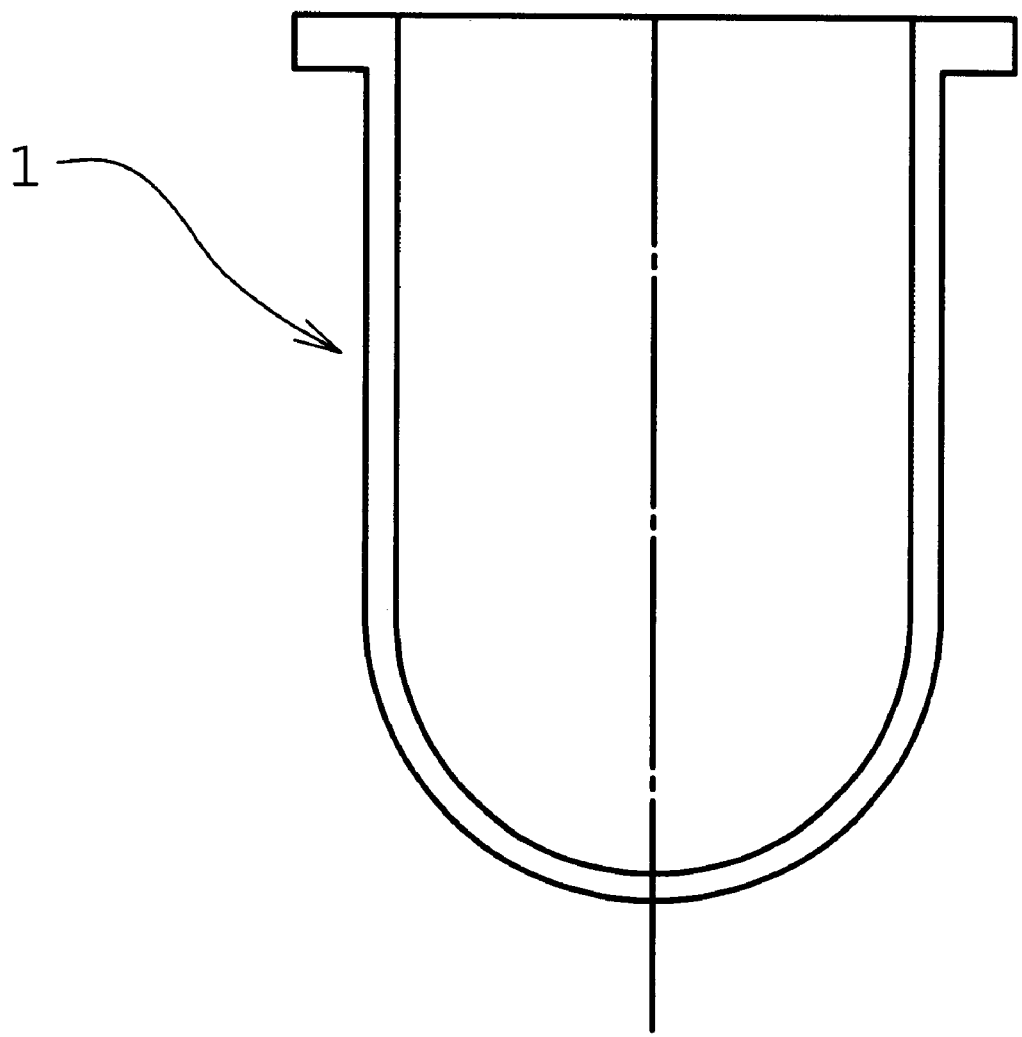
FIG. 1 is a cross section of a vessel used for determination of dissolution of drug into water in the present invention.

The present invention is described in detail in the following.

The intraoral adhesive preparation of the present invention consists of a support made of a cloth, and a pressure-sensitive adhesive layer containing a drug, which is formed on one side of this support.

The support to be used in the present invention is selected to be a cloth having a certain thickness, which is easy to handle, rich in flexibility, superior in the ability to follow uneven surfaces, and which substantially permits intraoral application. This is because a polymer film such as a poly(ethylene terephthalate) film and the like is thin and poor in handling property, and when it is highly stiff, is insufficient when following intraoral application site having convexes and concaves, which in turn causes a failure for a pressure-sensitive adhesive layer containing a drug to closely adhere to the application site, as well as consequent insufficient drug efficacy and marked discomfort at the application site.

The fiber constituting the cloth is not subject to any particular limitation and is exemplified by a synthetic fiber obtained from at least one kind of viscose rayon, cuprammonium rayon, diacetate, triacetate, nylon, poly(vinylidene chloride), poly(vinyl alcohol), poly(vinyl chloride), polyester, polyacrylonitrile, polyethylene, polypropylene, polyurethane, polyalkylene paraoxybenzoate, polychlal (1:1 mixture of vinyl chloride and poly(vinyl alcohol)) and the like; natural fiber such as cotton, wool, silk, hemp and the like; and the like. Of the above-mentioned fibers, a polyolefin fiber, such as polyethylene, polypropylene and the like, is preferable due to hydrophobicity. These fibers may be used alone or in combination. A split fiber consisting of two kinds of different components may be also used. The split fiber is a fiber of polypropylene and polyester obtained by dividing a conjugated fiber spun in a spinneret. The conjugated fiber is produced by extracting one component or by applying a strong impact, whereby to separate thinner fibers (i.e., split fibers), like sections of orange get separated when it is cut in thin slices.

The mode of the cloth may be a knitted fabric, a woven fabric, a nonwoven fabric and the like, and a nonwoven fabric, particularly a nonwoven fabric made of a polyolefin fiber of polyethylene, polypropylene and the like, is preferable from the economic aspect and the like.

While the production method of nonwoven fabric is not subject to any particular limitation, dry binder method, thermal bond method, spun bond method, spun-lace method, air lay process method, needle punch method, TCF method, Bemliese method, wet method, melt blown method and the like used for medical products are exemplified. Those produced according to the spun-lace method are preferably used from the aspects of degree of slip, safety and the like. The spun-laced nonwoven fabric is generally produced according to a production method for interlacing fibers without the use of a binder, such as spun lace, water punch, water jet, jet bond and the like.

The cloth preferably has a mass as defined in JIS-L1085 of 20 g/m$^2$–150 g/m$^2$, more preferably 50 g/m$^2$–120 g/m$^2$. When the mass is smaller than the above-mentioned range, the cloth becomes generally too soft to degrade the handling property of an adhesive preparation. While subject to change depending on the kind of the adhesive polymer constituting the pressure-sensitive adhesive layer, the pressure-sensitive adhesive layer containing the drug may strike through the support (extrusion from gaps between fibers constituting the support). Conversely, when it is greater than the above-mentioned range, the cushioning property becomes greater but the cloth becomes stiff as a whole and easily produces foreign sensation. When the mass is smaller than the above-mentioned range, the drug may leak from the back of the support due to saliva and the like (higher dissolution of the drug into water from the surface of the support without a pressure-sensitive adhesive layer).

Even if the mass of the cloth is within the above-mentioned range, when the fiber density thereof is too high, stretchability tends to decrease, making it difficult to follow uneven surfaces, and when it is too low, the interlace of the fiber becomes insufficient and allows easy omission of the fibers. The cloth preferably has a thickness as defined in JIS-L1085 of 0.1 mm–1.0 mm, more preferably 0.2 mm–0.8 mm. When the thickness is smaller than the above-mentioned range, the drug may leak from the back of the support due to saliva and the like (higher dissolution of the drug into water from the surface of the support without a pressure-sensitive adhesive layer).

The cloth preferably has a flex rigidity (by 45° cantilever method) as defined in JIS-L1085 of 10 mm–80 mm, more preferably 30 mm–70 mm. When the flex rigidity is within this value range, the medical adhesive sheet has preferable stiffness, further improving handling property during adhesion and adhesiveness of the adhesive preparation to uneven surfaces.

The above-mentioned cloth is selected such that it meets the requirements to be mentioned below, wherein the dissolution of the drug into water from the surface of a support, which surface not having a pressure-sensitive adhesive layer, after immersion in water at 32° C. for 20 minutes, is not more than 25 wt % of the total content of the drug.

The drug to be contained in the pressure-sensitive adhesive layer is not subject to any particular limitation as long as it permits substantially intraoral transmucosal administration. Examples of systemic drug include corticosteroids, analgesic inflammatory agent, hypnosedative, tranquilizer, antihypertensive agent, hypotensive diuretics, antibiotic, general anesthetic, antibacterial agent, antifungal agent, vitamin, coronary vasodilating agent, antihistaminic, antitussive, sex hormones, antidepressant, cerebral circulation improving agent, antiemetic drug, antitumor agent, enzyme, biological medicine and the like. Examples of local drug include local anesthetic such as lidocaine and the like, dental antibiotic such as tetracycline hydrochloride and the like, disinfectant such as cetylpyridinium chloride and the like, prophylactic and therapeutic agent for intraoral infection such as chlorhexidine hydrochloride and the like, antiphlogistic such as dimethylisopropylazulene and the like, adrenocortical hormones such as hydrocortisone acetate and the like, and the like. Preferably, at least one local anesthetic selected from the group consisting of cocaine, procaine, chloroprocaine, tetracaine, benzocaine, lidocaine, mepivacaine, prilocaine, bupivacaine, dibucaine, propoxycaine, etidocaine, diclonine, oxybuprocaine, tecaine, amethocaine, propitocaine, piperocaine, quatacaine, butacaine, meprylcaine, amylocaine, isobucaine, tricaine, parethoxycaine, pyrrocaine, hexylcaine, metabutoxycaine, xylocaine, oxethazaine, pyridoxine, dimethisoquin, ethyl aminobenzoate, ethyl piperidinoacetyl aminobenzoate, benzyl alcohol, chlorobutanol and pharmacologically acceptable salts thereof is used, and more preferably, lidocaine, lidocaine hydrochloride, procaine hydrochloride, mepivacaine hydrochloride, dibucaine hydrochloride, bupivacaine hydrochloride, propitocaine hydrochloride, tetracaine hydrochloride and tricaine hydrochloride are used.

The content of these drugs in the pressure-sensitive adhesive layer is determined as appropriate according to the kind of the drug, object of administration and the like. It is generally about 1–80 wt %, preferably about 2–70 wt %. When the content is less than 1 wt %, the release of the drug in an amount effective for the treatment or prevention is not achieved, whereas when it exceeds 80 wt %, the adhesive property is degraded to lose sufficient adhesion, which poses a limit on the therapeutic or prophylactic effect and is economically disadvantageous.

The drug is contained in the state of being dissolved in a pressure-sensitive adhesive layer, crystals precipitated therein by supersaturation, or being dispersed in a pressure-sensitive adhesive layer, depending on drug efficacy (object of use). In this way, an intraoral adhesive preparation for the treatment and/or prevention of various diseases can be obtained.

The pressure-sensitive adhesive layer is not subject to any particular limitation as long as it can substantially adhere to oral mucosa. It is formed using an adhesive wherein any polymer that shows pressure-sensitive adhesiveness at ordinary temperature is used as a base. A pressure-sensitive adhesive layer substantially insoluble in water or substantially water non-absorptive is preferable. In the present invention, by the "pressure-sensitive adhesive layer substantially insoluble in water or substantially water non-absorptive" is meant a pressure-sensitive adhesive layer formed using, as a main component, an adhesive polymer that shows solubility in water at 20° C. of not more than 5 wt % and shows pressure-sensitive adhesiveness at ordinary temperature and/or an adhesive polymer that shows absorption amount of water at 20° C. of not more than 5 wt % and shows pressure-sensitive adhesiveness at ordinary temperature. An adhesive to be used for a pressure-sensitive adhesive layer substantially insoluble in water or substantially water non-absorptive is exemplified by acrylic adhesive; rubber adhesives such as styrene-isoprene-styrene block copolymer, styrene-butadiene-styrene block copolymer, polyisoprene, polyisobutylene, polybutadiene and the like; silicone adhesives such as silicone rubber, dimethylsiloxane-based silicone, diphenylsiloxane-based silicone and the like; vinyl ether adhesives such as poly(vinyl methyl ether), poly(vinyl ethyl ether), poly(vinyl isobutyl ether) and the like; vinyl ester adhesives such as vinyl acetate-ethylene copolymer and the like; polyester adhesives comprising a carboxylic acid component (e.g., dimethyl terephthalate, dimethyl isophthalate, dimethyl phthalate etc.) and a polyhydric alcohol component (e.g., ethylene glycol etc.) and the like; and the like. Of these, an acrylic adhesive is preferable in view of a cloth anchor effect, adhesion to mucosa, drug solubility, drug stability and the like.

The above-mentioned acrylic adhesive is obtained by copolymerizing alkyl (meth)acrylate as a main component with a functional monomer. The alkyl (meth)acrylate is exemplified by alkyl (meth)acrylate wherein the alkyl group thereof is a straight-chain alkyl group or branched-chain alkyl group having 4 to 13 carbon atoms, such as butyl, pentyl, hexyl, heptyl, octyl, 2-ethylhexyl, nonyl, decyl, undecyl, dodecyl, tridecyl and the like, wherein these can be used alone or in combination.

The functional monomer to be copolymerized with the above-mentioned alkyl (meth)acrylate has at least one unsaturated double bond involved in the copolymerization reaction in a molecule and a functional group in the side chain. Examples of such functional monomer include carboxyl group-containing monomers such as (meth)acrylic acid, itaconic acid, maleic acid, maleic anhydride and the like; hydroxyl group-containing monomers such as hydroxyethyl (meth)acrylate, hydroxypropyl (meth)acrylate and the like; sulfo group-containing monomers such as styrenesulfonic acid, allylsulfonic acid, sulfopropyl (meth)acrylate, (meth)acryloyloxynaphthalene sulfonic acid, acrylamide methylpropanesulfonic acid and the like; amino group-containing monomers such as aminoethyl (meth)acrylate, dimethylaminoethyl (meth)acrylate, tert-butylaminoethyl (meth)acrylate and the like; amide group-containing monomers such as (meth)acrylamide, dimethyl(meth)acrylamide, N-methylol (meth)acrylamide, N-methylolpropane(meth)acrylamide, N-vinylacetamide and the like; alkoxyl group-containing monomers such as methoxyethyl (meth)acrylate, ethoxyethyl (meth)acrylate, methoxyethylene glycol (meth) acrylate, methoxydiethylene glycol (meth)acrylate, methoxypolyethylene glycol (meth)acrylate, methoxypolypropylene glycol (meth)acrylate, tetrahydrofuryl (meth)acrylate and the like; and the like. Besides these, examples of the copolymerizable monomer include (meth) acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrrole, vinylimidazole, vinylcaprolactam, vinyloxazole, vinylmorpholine and the like.

As far as the characteristics of the present invention are not adversely affected, alkyl (meth)acrylate having alkyl group having 1 to 3 or 14 or more carbon atoms may be copolymerized.

The acrylic adhesive in the present invention is preferably a copolymer of alkyl (meth)acrylate and (meth)acrylic acid, particularly a copolymer obtained by polymerizing alkyl (meth)acrylate (65–99 wt %) and (meth)acrylic acid (1–35 wt %), because they are particularly superior in pressure-sensitive adhesiveness and cohesion property as the adhesive property, release property of drug contained in a pressure-sensitive adhesive layer and the like.

In the present invention, the adhesive polymer (adhesive) constituting the pressure-sensitive adhesive layer is determined to achieve the object of administration of the drug. When administration in a short time is desired, an adhesive polymer superior in release of the contained drug is selected, and when administration for a long time is desired, an adhesive polymer capable of relatively sustained release of the contained drug is selected.

The above-mentioned pressure-sensitive adhesive layer may contain various additives as necessary. Examples of the additive include plasticizer, absorption promoter, antioxidant, tackifier, filler and the like. The plasticizer can control adhesion to oral mucosa by plasticizing the pressure-sensitive adhesive layer. Examples of the plasticizer include hydrocarbons (e.g., liquid paraffin etc.), diisopropyl adipate, diethyl sebacate and the like, which may be used alone or in combination. The absorption promoter enhances solubility and diffusibility of the drug in the pressure-sensitive adhesive layer. The compound that enhances solubility of a drug includes glycols such as ethylene glycol, diethylene glycol, propylene glycol, triethylene glycol, polyethylene glycol, polypropylene glycol and the like, and the like. A compound that mainly enhances diffusibility of the drug includes fats and oils such as olive oil, castor oil, squalane, lanolin and the like, and the like. Examples of the antioxidant include ascorbic acid, tocopherol acetate, butylhydroxyanisole, dibutylhydroxytoluene, propyl gallate, 2-mercaptobenzimidazole and the like. Examples of the tackifier include rosin, denatured rosin, petroleum resin, polyterpene resin, polystyrene resin, polybutene resin, liquid polyisobutylene and the like. Examples of the filler include kaolin, titanium oxide, talc, calcium carbonate, magnesium carbonate, silicate, silicic acid, magnesium aluminate metasilicate, aluminum hydrate, barium sulfate, calcium sulfate and the like. Examples of other additives include various surfactants, ethoxylated stearyl alcohol, glycerin monoesters (e.g., glycerin monooleate, glycerin monocaprylate, lauryl monoglyceride and the like), glycerin diester, glycerin triester or a mixture thereof, higher fatty acid esters such as ethyl laurylate, isopropyl myristate, isotridecyl myristate, octyl palmitate, isopropyl palmitate, ethyl oleate, diisopropyl adipate and the like, higher fatty acids such as oleic acid, caprylic acid and the like, N-methylpyrrolidone, 1,3-butanediol and the like.

The production method of the intraoral adhesive preparation of the present invention is not subject to any particular limitation. For example, a drug, an adhesive polymer and the like are dissolved or dispersed in a solvent, the obtained solution or dispersion is applied onto one surface of a support, and dried to form a pressure-sensitive adhesive layer on one surface of the support. It is also produced by applying the above-mentioned solution or dispersion onto a protective release liner, drying same to form a pressure-sensitive adhesive layer on the release liner, and adhering the pressure-sensitive adhesive layer on the release liner to a support. In this case, unexpected contact with and adhesion of the pressure-sensitive adhesive layer to an instrument, container and the like during production, transport or storage can be prevented. It is also possible to protect the exposed surface of a pressure-sensitive adhesive layer by applying a release liner until immediately before adhesion to oral mucosa, and separating the release liner when adhering to the oral mucosa to expose the pressure-sensitive adhesive layer for adhesion, whereby degradation of the adhesive property of the pressure-sensitive adhesive layer and deterioration of the drug can be prevented.

The material of the release liner is not subject to any particular limitation as far as it can be released easily from the pressure-sensitive adhesive layer when in use. For example, a synthetic resin film made from polyester, poly (vinyl chloride), poly(vinylidene chloride), poly(ethylene terephthalate) and the like, paper such as wood free paper, glassine paper and the like, a laminate film of wood free paper or glassine paper and the like and a polyolefin film, and the like are used, wherein the surface to be in contact with the pressure-sensitive adhesive layer is covered with silicone resin, fluorocarbon resin and the like for release treatment. The release liner has a thickness of generally 10–200 μm, preferably 50–100 μm.

The pressure-sensitive adhesive layer has a thickness of generally 10 μm–200 μm, preferably 15 μm–150 μm.

The shape of the intraoral adhesive preparation of the present invention is not subject to any particular limitation as long as it can be adhered substantially. For example, it may be circle, ellipse, rectangle, square, triangle, hexagon and the like. Particularly it is preferably ellipse, rectangle or square from the aspects of production and use. The size should be suitable for intraoral adhesion, and may be, for example, in the case of ellipse, the minor axis is generally 0.5 cm–2 cm, preferably 0.8 cm–1.5 cm, and the major axis is 1 cm–5 cm, preferably 2 cm–4 cm. When it is rectangle, the short side is generally 0.5 cm–2 cm, preferably 0.8 cm–1.5 cm, and the long side is 1 cm–5 cm, preferably 2 cm–4 cm. When it is square, the side thereof is generally 0.5 cm–2 cm, preferably 0.8 cm–1.5 cm.

The intraoral adhesive preparation of the present invention shows dissolution of a drug into water from the surface of the support, which surface being free of a pressure-sensitive adhesive layer, after immersion in water at 32° C. for 20 minutes, of not more than 25 wt %, preferably not more than 10 wt %, of the total content of the drug. When the dissolution of the drug into water exceeds 25 wt %, leakage of drug due to saliva and the like tends to occur easily, making patients unnecessarily feel uncomfortable with bitterness and the like, and decreasing the utilization efficiency of the drug to lose sufficient drug efficacy. In the context of the present invention, "the surface of the support, which surface being free of a pressure-sensitive adhesive layer" means a surface of the support opposite from the surface having a pressure-sensitive adhesive layer and the side surface(s) of the support. The above-mentioned dissolution of the drug into water is measured according to the dissolution test method (puddle method) defined in the Japan Pharmacopoeia.

To make the dissolution of the drug into water fall within the above-mentioned range, the mode of the cloth (e.g., nonwoven fabric), material (e.g., polyolefin), thickness, mass, kind of adhesive (e.g., acrylic adhesive), thickness of pressure-sensitive adhesive layer and the like are appropriately determined.

The intraoral adhesive preparation of the present invention preferably has a flex rigidity (by 45° cantilever method) as defined in JIS-L1085 of 15 mm–60 mm, more preferably 20 mm–50 mm, for the balance between handling property and feel during use. When the flex rigidity exceeds this range and is smaller, handling property tends to be degraded. For example, intraoral adhering of the sheet to a complicated and narrow space, as formed by dental part, tongue part and the like, tends to become difficult. When it is outside this range and is larger, a sense of foreign matter tends to occur easily upon application.

When the intraoral adhesive preparation of the present invention is prepared into an intraoral adhesive preparation containing a local drug, it is mainly adhered to gingiva to allow immediate expression of the drug efficacy. When the intraoral adhesive preparation of the present invention is prepared into an intraoral adhesive preparation containing a systemic drug, it is adhered to mucobuccal, labial mucosa, hypoglottis, gingiva and the like, where the drug efficacy is maintained for tens of minutes to several hours. When the intraoral adhesive preparation containing a systemic drug of the present invention is adhered to upper labial mucosa or the outside of maxillary gingiva, the drug efficacy is maintained for a long time because contact with saliva is less, and the sheet is press-held by the labium and the gum.

The present invention is explained in detail in the following by referring to examples. The present invention is not limited by these examples in any way. In the following description, "parts" means "parts by weight" and the thickness and mass of a nonwoven fabric are measured according to the method defined in JIS-L1085.

Preparation of Adhesive Solution A

2-Ethylhexyl acrylate (95 parts) and acrylic acid (5 parts) were copolymerized in ethyl acetate under an inert gas atmosphere to prepare an adhesive solution A.

EXAMPLE 1

Lidocaine (60 parts) was added to adhesive solution A (40 parts, solids) and mixed for dissolution. The obtained solution was applied on a polyester film (thickness 75 $\mu$m) after a release treatment so that the thickness after drying would be about 20 $\mu$m, and dried to give a pressure-sensitive adhesive layer. Then, this pressure-sensitive adhesive layer was adhered to a stretch polypropylene nonwoven fabric (thickness 0.6 mm, mass: 100 g/m$^2$) prepared by a spun-lace method to give an intraoral adhesive preparation.

EXAMPLE 2

Lidocaine (60 parts) was added to adhesive solution A (40 parts, solids) and mixed for dissolution. The obtained solution was applied on a polyester film (thickness 75 $\mu$m) after a release treatment so that the thickness after drying would be about 20 $\mu$m, and dried to give a pressure-sensitive adhesive layer. Then, this pressure-sensitive adhesive layer was adhered to a nonwoven fabric (thickness 0.42 mm, mass: 90 g/m$^2$) made of split fibers, which was obtained by interlacing split fibers obtained by dividing a conjugated fiber (polypropylene content: 55 wt %, polyester content: 45 wt %) by a spun-lace method to give an intraoral adhesive preparation.

Comparative Example 1

Lidocaine (60 parts) was added to adhesive solution A (40 parts, solids) and mixed for dissolution. The obtained solution was applied on a polyester film (thickness 75 $\mu$m) after a release treatment so that the thickness after drying would be about 20 $\mu$m, and dried to give a pressure-sensitive adhesive layer. Then, this pressure-sensitive adhesive layer was adhered to a stretch polyester nonwoven fabric (thickness 0.6 mm, mass: 100 g/m$^2$) prepared by a spun-lace method to give an intraoral adhesive preparation.

Comparative Example 2

Lidocaine (60 parts) was added to adhesive solution A (40 parts, solids) and mixed for dissolution. The obtained solution was applied on a polyester film (thickness 75 $\mu$m) after a release treatment so that the thickness after drying would be about 20 $\mu$m, and dried to give a pressure-sensitive adhesive layer. Then, this pressure-sensitive adhesive layer was adhered to a polyester nonwoven fabric (thickness 0.035 mm, mass: 12 g/m$^2$) to give an intraoral adhesive preparation.

Comparative Example 3

Lidocaine (60 parts) was added to adhesive solution A (40 parts, solids) and mixed for dissolution. The obtained solution was applied on a polyester film (thickness 75 $\mu$m) after a release treatment so that the thickness after drying would be about 20 $\mu$m, and dried to give a pressure-sensitive adhesive layer. Then, this pressure-sensitive adhesive layer was adhered to a polypropylene nonwoven fabric (thickness 0.2 mm, mass: 18 g/m$^2$) to give an intraoral adhesive preparation.

The intraoral adhesive preparations obtained in the above-mentioned Examples 1, 2 and Comparative Examples 1, 2, 3 were cut into 1 cm$^2$(1 cm×1 cm) to give test pieces and subjected to property evaluation of the following (1) and (2). The results are shown in Tables 1 and 2.

(1) Dissolution of drug into water

Figure 2A:
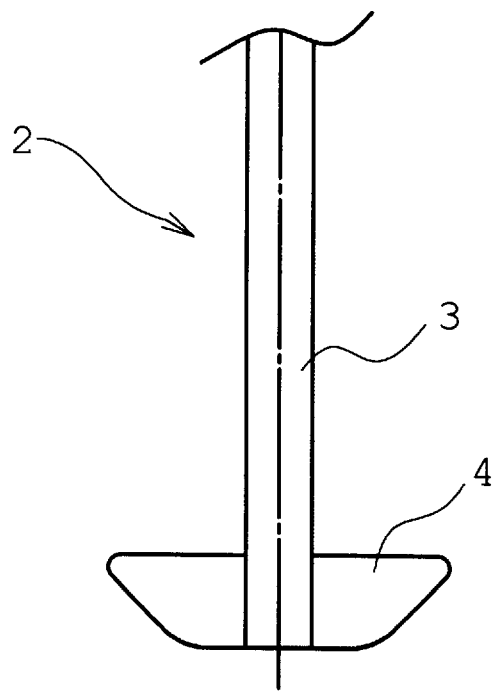
FIG. 2(a) is a front view and FIG. 2(b) is a side view of a puddle used for determination of dissolution of drug into water in the present invention.
Figure 2B:
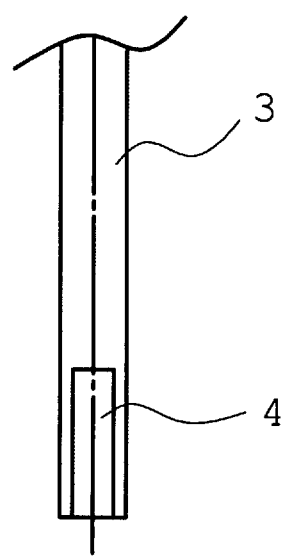

The above-mentioned test pieces were determined for dissolution of drug into water according to dissolution test method (puddle method) described in the Japan Pharmacopoeia. A container (FIG. 1) was set in a dissolution tester (NTR-VS6P; TOYAMA SANGYO CO., LTD.) and 500 mL of water was charged as an eluent in this container. The dissolution tester was set to 32° C. and maintained at this temperature. A test piece stripped of a polyester film was fixed with a double bond tape (No.500; NITTO DENKO CORPORATION) in the center of a stainless steel board (diameter 41.2 mm, thickness 3.3 mm) with the pressure-sensitive adhesive layer containing a drug facing down, and immersed in water in the container. A puddle (FIG. 2) was set in the container and rotated at 25 rotations/min to agitate the eluent. After 20 minutes, the eluent (5 mL) was taken from the container. The amount of the drug dissolved in the obtained eluent was measured by liquid chromatography, based on which the percentage of dissolution relative to the initial drug content was calculated.

TABLE 1

| | dissolution (wt %) of drug into water after 20 minutes |
|---|---|
| Example 1 | 4.2 |
| Example 2 | 21.6 |
| Comparative Example 1 | 30.6 |
| Comparative Example 2 | 74.2 |
| Comparative Example 3 | 68.0 |

(2) Leakage of drug due to saliva

A test piece stripped of a polyester film was adhered to the inside of maxillary gingival (gently dried beforehand with absorbent cotton) of 5 volunteers, and the bitterness and pharmacological effect during use was evaluated according to the following numerical criteria.

Bitterness During Use

The support of the test piece (adhesive sheet) was tasted with the tip of the tongue wet with saliva every 30 seconds for 3 minutes after adhesion to evaluate the bitterness due to the drug and evaluated according to the following numerical criteria.
0: bitterness felt within 1 minute after adhesion
1: bitterness felt after 1 minute and within 3 minutes from adhesion
2: bitterness not felt even after 3 minutes from adhesion Pharmacological Effect The test piece (adhesive sheet) was adhered and peeled off 3 minutes later. The application site was stimulated with a syringe needle and the anesthetic effect was evaluated according to the following numerical criteria.
0: pain was felt
1: slight pain was felt
2: pain was not felt

TABLE 2

| | Evaluation items | |
|---|---|---|
| | bitterness[1] during use | Pharmacological effect[1] |
| Example 1 | 2.0 | 2.0 |
| Example 2 | 2.0 | 2.0 |
| Comparative Example 1 | 0.6 | 1.6 |
| Comparative Example 2 | 0.0 | 0.8 |
| Comparative Example 3 | 0.2 | 1.0 |

[1]average evaluation point of 5 volunteers

From Tables 1 and 2, it is evident that the intraoral adhesive preparations of Examples 1 and 2 showed low percentage of dissolution of the drug into water, and therefore, the drug did not leak out due to saliva, bitterness was not felt very much, and the pharmacological effect was sufficient. On the other hand, because the adhesive sheet of Comparative Example 1 comprised a polyester nonwoven fabric, because the adhesive sheet of Comparative Example 2 had smaller thickness and mass of the nonwoven fabric, and because the adhesive sheet of Comparative Example 3 had a small mass of the nonwoven fabric, the dissolution of the drug into water was high, and therefore, the drug leaked out due to saliva, bitterness was felt, and the pharmacological effect was not sufficient.

According to the present invention, an intraoral adhesive preparation can be obtained, which comprises a support made of a cloth, and a pressure-sensitive adhesive layer containing a drug, which is formed on one surface of the support. The intraoral adhesive preparation of the present invention shows dissolution of the drug into water from the surface of the support, which surface being free of a pressure-sensitive adhesive layer, when immersed in water at 32° C. for 20 minutes of not more than 25 wt % of the entire content of the drug. As a result, drug leakage due to saliva and the like does not occur easily, which in turn eliminates unnecessary bitterness and the like felt by the patients, and maintains the utilization efficiency of the drug.

This application is based on a patent application Ser. No. 2000-254434 filed in Japan, the contents of which are hereby incorporated by reference.

What is claimed is:

1. An intraoral adhesive preparation comprising a support made of a cloth, and a pressure-sensitive adhesive layer containing a drug, which is formed on one surface of the support, wherein the dissolution of the drug into water from the surface of the support, which surface being free of a pressure-sensitive adhesive layer, after immersion in water at 32° C. for 20 minutes, is not more than 25 wt % of the total content of the drug.

2. The intraoral adhesive preparation of claim 1, wherein the cloth has a mass of 20–150 g/m$^2$.

3. The intraoral adhesive preparation of claim 1, wherein the cloth has a thickness of 0.1–1.0 mm.

4. The intraoral adhesive preparation of claim 1, wherein the cloth is a nonwoven fabric.

5. The intraoral adhesive preparation of claim 4, wherein the nonwoven fabric is produced by a spun-lace method.

6. The intraoral adhesive preparation of claim 4, wherein the nonwoven fabric mainly comprises a polyolefin fiber.

7. The intraoral adhesive preparation of claim 1, wherein the drug is a local anesthetic.

* * * * *